(12) United States Patent
Cardamone (10) Patent No.: US 8,530,626 B1
(45) Date of Patent: Sep. 10, 2013

(54) METHODS TO PRODUCE KERATIN ELASTOMER

(75) Inventor: Jeanette M. Cardamone, Lafayette Hill, PA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 62 days.

(21) Appl. No.: 13/106,942

(22) Filed: May 13, 2011

(51) Int. Cl.
*A61K 38/17* (2006.01)

(52) U.S. Cl.
USPC ............ 530/357; 530/350; 530/409; 530/410

(58) Field of Classification Search
USPC .................................. 530/357, 350, 409, 410
See application file for complete search history.

(56) References Cited

U.S. PATENT DOCUMENTS 3,619,117 A * 11/1971 Anzuino et al. ............... 8/137.5
4,144,027 A * 3/1979 Habib .............................. 8/127.6
6,914,126 B2 * 7/2005 Van Dyke .................... 530/357

FOREIGN PATENT DOCUMENTS

JP         EP1353005       10/2003

* cited by examiner

*Primary Examiner* — Chih-Min Kam
(74) *Attorney, Agent, or Firm* — John D. Fado; G. Byron Stover; Gail E. Poulos (57) ABSTRACT

Methods to produce keratin elastomer, involving:
(A)(1) reacting a diisocyanate with a blocking agent to form a diisocyanate with one —NCO group blocked by the blocking agent and one —NCO group unblocked,
(2) reacting the diisocyanate with one —NCO group blocked by the blocking agent and one —NCO group unblocked with keratin at about 100° to about 120° C. to form keratin urethane with —NCO group functionality (i.e., with one —NCO group unblocked),
(3) optionally reacting the keratin urethane with —NCO group functionality with a compound capable of reacting with the —NCO group;
(B) reacting a diisocyanate with keratin to form keratin elastomer; or
(C) reacting a monoisocyanate with keratin to form keratin elastomer.

9 Claims, 8 Drawing Sheets

METHODS TO PRODUCE KERATIN ELASTOMER

BACKGROUND OF THE INVENTION

The present invention relates to methods to produce keratin elastomer, involving:
(A)(1) reacting a diisocyanate with a blocking agent to form a diisocyanate with one —NCO group blocked by the blocking agent and one —NCO group unblocked,
(2) reacting the diisocyanate with one —NCO group blocked by the blocking agent and one —NCO group unblocked with keratin at about 100° to about 120° C. to form keratin urethane with —NCO group functionality (i.e., with one —NCO group unblocked),
(3) optionally reacting the keratin urethane with —NCO group functionality with a compound capable of reacting with the —NCO group;
(B) reacting a diisocyanate with keratin to form keratin elastomer; or
(C) reacting a monoisocyanate with keratin to form keratin elastomer.

Isocyanates were discovered by Wurtz in 1849 and their uses in polyurethane (PU) began in 1937. Polyurethane plastics are produced by the condensation reaction of a polyol and a diisocyanate to form carbamate, the chemical unit in elastomers. Polyurethanes are the major products in which isocyanates are used. For example, 4,4-methylene bis (isocyanatocyclohexane) was reacted with various polyols such as polyethylene glycol (PEG) to form a film coating to waterproof textiles (Tsai, H.-C., et al., Textile Research J., 77(9): 710-720 (2007)). Diisocyanates and low molecular weight diols and amines react to form polyurethane through crosslinking where the product has hard and soft domains that determine modulus, toughness, and creep resistance. Themoplastic polyurethanes exhibit high toughness and abrasion resistance, and are synthesized from three principal reactants: a difunctional polyol $HO(RO)_xH$ which determines soft segment length, a difunctional chain extender HOR'OH, which determines hard segment structure, and a diisocyanate (1+y) OCNR"NCO reacting agent. The urethane product combines hard and soft segments along the polyurethane linear molecular chain through carbamate linkages with the hard and soft segments determining mechanical properties of the product.

Diisocyanates were used to couple two proteins, bovine serum albumin (BSA) and bovine gamma globulin (BGG). Urethane-based castor oil was synthesized with free isocyanate groups to react with amino groups present in biological systems to form products for surgical adhesives used for haemostasis, sealing air leakage, and tissue adhesion in wound mediation. These bio-based adhesives were biodegradable and biocompatible (Ferreira, P., et al., Biological Macromolecules, 40: 144-152 (2007)). Reactive polyisocyanates systems were formed from PU prepolymer and microencapsulated isophorone diisocyanate healing agent as an active and responsive system for self-healing. In this system, toluene diisocyanate (TDI) was reacted with chain extender, 1,4-butanediol, to form a prepolymer for subsequent encapsulation of isophorone diisocyanate, a monomeric aliphatic diisocyanate used in abrasion and UV resistant coatings (Yang, J., et al., Macromolecules, 41: 9650-9655 (2008)). Biobased polyurethane was derived from canola oil derived polyols and diisocyanate as a substitute for petrochemical derivatives (Hojabri, L., et al., Biomacromolecules, 10: 884-891 (2009); U.S. Pat. No. 3,691,225). Biomedical polyurethane was synthesized as segmented polyether polyurethane containing hard segments of urea and soft segments of polyether linked by the urethane group for orthopedic implant applications (Wong, E. W., Development of a Biomedical Polyurethane, In: Urethane Chemistry and Applications, K. N. Edwards, Ed., ACS Symposium Series 172, Chapter 31, "Development of a Biomedical Polyurethane," pages 489-502, 1981). Hydrogels were prepared by the reaction of chitosan with blocked diisocyanate for uses as scaffolds for tissue engineered medical products (Lin-Gibson, S., et al., Carbohydrate Polymers, 54: 193-199 (2003)).

We have produced a bio-based keratin elastomer which can be reacted with other compounds (e.g., poly(ethylene glycol)) through the amino terminus of the keratin protein in order to produce compounds which can provide high value-added keratin-based materials for cosmetic and biomedical applications.

SUMMARY OF THE INVENTION

In accordance with the present invention there is provided a method to produce keratin elastomer, involving:
(A)(1) reacting a diisocyanate with a blocking agent to form a diisocyanate with one —NCO group blocked by the blocking agent and one —NCO group unblocked,
(2) reacting the diisocyanate with one —NCO group blocked by the blocking agent and one —NCO group unblocked with keratin at about 100° to about 120° C. to form keratin urethane with —NCO group functionality (i.e., with one —NCO group unblocked),
(3) optionally reacting the keratin urethane with —NCO group functionality with a compound capable of reacting with the —NCO group;
(B) reacting a diisocyanate with keratin to form keratin elastomer; or
(C) reacting a monoisocyanate with keratin to form keratin elastomer.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

DETAILED DESCRIPTION OF THE INVENTION

Keratin elastomer can be formed using synthesis methods involving monoisocyanates (—NCO) or diisocyanates (—NCO)$_2$ in compounds having R' and R" organic moieties where R' and R" denote different hydrocarbon attachments or side chains.

Figure 1:
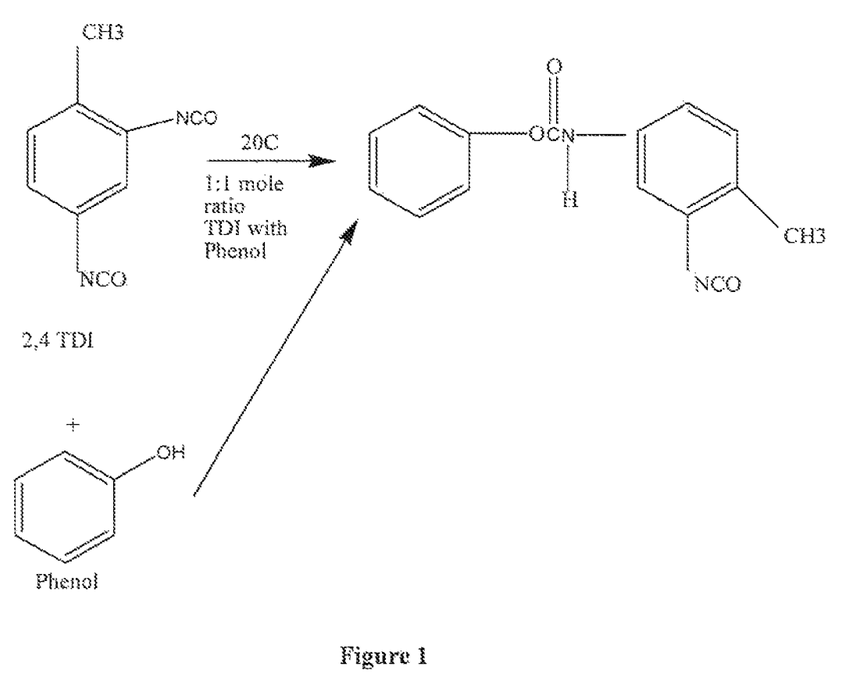
FIG. 1 shows synthesis of blocked isocyanate, phenyl N-(3-cyanato-4-methylphenyl carbamate as described below.

One method using diisocyanates involves two-step keratin elastomer formation utilizing a precursor synthesized from a blocking agent like phenol (see, for example, FIG. 1). In the first step, diisocyanate (R—(—NCO)$_2$ where "R" is an organic moiety) is reacted with a blocking agent (e.g., phenol) to form the monosubstituted precursor product [P—O—(C=O)—NH—R—NCO). In the second step, the precursor product is reacted with keratin (in powder or hydrolysate form) generally at about 100° to about 120° C. (e.g., 100° to 120° C.) whereby keratin replaces the blocking agent (e.g., phenol) to form keratin elastomer (K—O—(C=O—NH)—R—NCO). An optional third step (not shown in FIG. 1) involves reacting (K—O—(C=O)—NH—R—NCO) with, for example, a compound capable of reacting with the cyanate group, for example glycol, to form keratin elastomer (K—O—(C=O)—NH—R—O—(C=O)—NH—G). Alternative to glycol include but are not limited to the following:

Alcohols such as aliphatic, cycloaliphatic or aromatic mono-, di-, and trihydroxyl compounds and alcohol ethers such as alcohols, alcohol esters, hexahydroxycylcohexane, including aromatic compounds such as di- and trihydroxybenzene including polyalkane, polycycloalkane, and polyaromatic-derived polyhydric alcohols, and the like. Preferred compounds include aliphatic, cycloaliphatic, and trihydroxyl alcohols.

Polyols or polyhydric alcohols, such as ethylene glycol, propane-1,2- and/or -1,3-diol, butane-1,4- and/or -2,3-diol, hexane-1,6-diol, neopentyl glycol, 1,4-bis-hydroxymethyl-cyclohexane, 2-methyl-propane-1,3-diol, glycerol, trimethylolpropane, hexane-1,2,6-triol, pentaerythritol, quinitol, mannitol and sorbitol, formitol, methylglycoside, and di-, tri-, tetra- and higher diols of polyoxyethylene, polyoxypropylene and polyoxybutylene, and other polyhydroxyl compounds, poly(ethylene glycol), poly(tetramethylene glycol), glycerol, polyoxyethylenes of the formula $NH_2(CH_2CH_2O)_x$H where "x" ranges from 10 to 200, polyether polyol adducts (polyoxyalkylene diol) such as polyethylene glycol, polypropylene glycol, or polybutylene glycol of about 4,000 to 20,000 molecular weight such as pentaerythritol, neopentyl glycol, trimethylolpropane, trimethylolethane, and dimethylolpropionic acid, polyether polyol, polyhydric alcohol ether aliphatic, cycloaliphatic, or aromatic mono-, di-, tri, polyhydric alcohols, and alkane-1,2,3-triols such as 1,2,3-Propanetriol, and polyglycerols (tri-, hexa-, and decoglycerols), cycloaliphatic polyhydric compounds such as cyclopentandiol-1,2,1,4-cyclohexandiol, and their adducts, and amine counterparts, and hydroxyl-counterparts of carboxylates, sulfhydryl compounds and/or ether alcohols, and/or mono-, di-, tricarboxy polyalkanes, alkenes, and various polyfunctional polyesters or polyester polyols, polyether polyols or polyalkylene ether polyalcohols are preferred, and these include polyethlene glycols, polypropylene glycols, polyhexamethylene ether glycols and the like. Preferred compounds include ethylene glycol, propane-1,2- and/or -1,3-diol, butane-1,4- and/or -2,3-diol, hexane-1,6-diol, neopentyl glycol, polyhydric alcohols, and alkane-1,2,3-triols such as 1,2,3-Propanetriol, and polyglycerols (tri-, hexa-, and decoglycerols), polypropylene glycols.

Hydroxy amines and amine diols, polyhydric alcohol amine or their mixtures, including bi- and tri-functional compounds containing hydroxyl amines and mono-, di, tri, polyamines, and amine counterparts of carboxylates, sulfhydryl compounds and/or ether alcohols with mono-, di-, and tri-carboxypolyalkanes, or their alkenes or cycloalkanes, and/or hydroxyl functions. Preferred compounds include polyhydric alcohol amine, ethylene glycol, propane-1,2- and/or -1,3-diol.

Amines, mono-di, tri-functional alkane, cycloalkane, aromatic alkanolamines such as ethanolamine, diethanolamine, and triethanolamine, mono- di-, tri-functional cyclo- and aryalkanolamines, mono- di-, tri-functional aromatic amines, and their ethers, hydroxyl, diol, ether, diol ether, and esters, as monomers and/or polymers. Preferred compounds include ethanolamine, diethanolamine, and triethanolamine, mono- di-, tri-functional cyclo- and aryalkanolamines.

Thiols, or sulfhydryl compounds, include polyhydric polyalkylene thioethers, 2-mercaptoethanol derivatives such as 2-mercaptoethyl ether, thiol-terminated prepolymers such as, 1,6-Hexane dithiol, alkane, alkane dithiols having a chain-length of from two to 20 carbon atoms, alkene diols, alkene dithiols, cycloalkylene diols, cycloalkylene dithiols, aromatic dithiols. Preferred compounds include polyhydric polyalkylene thioethers AND polyhydric polyalkylene thioethers.

Acids and polycarboxylic acids and derivatives may be aliphatic, cycloaliphatic, aromatic and/or heterocyclic and they may be substituted, e.g. by halogen atoms, and/or unsaturated, optionally, adipic acid, sebacic acid, phthalic acid anhydride, tetrahydro- and hexahydro-phthalic acid anhydride, isophthalic acid, trimellitic acid, maleic acid anhydride, dimerized and trimerized unsaturated fatty acids, dimethylterephthalate and terephthalic acid-bis-glycol ester. The polycarboxylic acids can be aliphatic, cycloaliphatic, aromatic and/or heterocyclic, and can optionally be substituted, for example, by halogen atoms, and/or they can be unsaturated. Examples of these polycarboxylic acids are succinic acid, azelaic acid, sebacic acid, phthalic acid, isophthalic acid, trimellitic acid, and their anhydrides: phthalic acid anhydride, tetrahydrophthalic acid anhydride, hexahydrophthalic acid anhydride, tetrachlorphthalic acid anhydride, endomethylene tetrahydrophthalic acid anhydride, glutaric acid anhydride, including maleic acid, maleic acid anhydride, fumaric acid, dimeric and trimeric fatty acids, such as oleic acid, optionally in admixture with monomeric fatty acids, terephthalic acid dimethyl ester, terephthalic acid-bis-glycol ester. Preferred compounds include adipic acid, sebacic acid, phthalic acid anhydride.

Mono- and diisocyanates which may be used in the present invention include but are not limited to the following: alkyl or aryl monoisocyanate such as 4,4'-dicyclohexylmethane diisocyanate, 1-isocyanato-3,3,5-trimethyl-5-isocyanatomethyl cyclohexane (isophorone diisocyanate), 4,4'-diioscyanato dicyclohexylmethane, hexamethylene diisocyanate, isophorone diisocyanate, 4,4'-diphenylmethane diisocyanate, hexamethylene monoisocyanate, benzyl isocyanate, o- and p-toluene monoisocyanate, or phenylisocyanates, methylenebis(phenylisocyanate, or diisocyanates such as toluene 2,4 or 2,6-diisocyanate (TDI/2,4-diisocyanate-1-methybenzyne, toluene 2,6-diisocyanate (TDI) in ratios 65:35 and 80:20 mixtures of toluene 2,4 and 2,6-diisocyanate; 4,4'-diphenyl methane diisocyanate (MDI)/1,1'-methylenebis(4-isocyanathobenzene); 2,4'-diphenyl methane diisocyanate (MDI)/1-isocyanato-2-(4-isocyanatophenyl)methylbenzene; 2,2'-diphenyl methane diisocyanate (MDI)/1,1'-methylenebis(2-isocyanatobenzene), 1,6-hexamethylene diisocyanate (HDI)/1,6-diisocyanatohexane; isophorone diisocyanate (PDI)/5-isocyabato-1-(isocyanatomethyl)-1,3,3-trimethylcyclohexane; m-tetramethylxylene diisocyanate)m-TMXDI)/1,3-bis(1-isocyanato-1-methylethyl)benzene; dicyclohexylmethane 4,4'-diisocyanate(HMDI)/1,1'-methylbis(4-isocyanatocyclohexane); triphenylmethane-4,4',4"-triisocyanate/1,1',1"-methylidynetris(4-isocyanatobenzene); naphthalene 1,5-diisocyanate (NDI)/1,5-diisocyanatonaphthalene; p-phenylene diisocyanate (PPDI)/1,4-diisocyanatobenzene, 1,4-tetramethylene diisocyanate, 2,2,4-trimethyl-1,6-diisocyanatohexane, 1,10-decamethylene diisocyanate, 1,4-cyclohexylene diisocyanate, 4,4'-methylenebis(isocyanatocyclohexane), 1-isocyanato-3-isocyanatomethyl-3,5,5-trimethylcyclohexane, m- and p-phenylene diisocyanate, xylene diisocyanate, 4-chloro-1,3-phenylene diisocyanate, 1,5-naphthalene diisocyanate, 1,5-tetrahydronaphthalene diisocyanate; and the like. aliphatic diisocyanates, such as ethylene diisocyanate, trimethylene diisocyanates, tetramethylene diisocyanate, hexamethylene diisocyanate, propylene-1,2-diisocyanate, butylene-1,2-diisocyanate, and butylene-2,3-diisocyanate; alkylidene diisocyanates, such as ethylidine diisocyanate and butylidine diisocyanate; cycloalkylene diisocyanates such as cyclopentylene-1,3-diisocyanate, and cyclohexylene-1,4-diisocyanate; cycloalkylidene diisocyanates, such as cyclopentylidene diisocyanate and cyclohexylidene diisocyanate; aromatic diisocyanates such as m-phenylene diisocyanate; p-phenylene diisocyanate, polymethylene polyphenylisocyanate, 2,4-tolylene diisocyanate, 2,6-tolylene diisocyanate, dianisidine diisocyanate, bitolylene diisocyanate, naphthalene-1,4-diisocyanate, and diphenylene-4,4'-diisocyanate; aliphatic-aromatic diisocyanates such as xylylene-1,3-diisocyanate, bis(4-isocyanatophenyl)methane, and 4,4'-diphenylpropane diisocyanate; durylene diisocyanate; naphthalene triisocyanate and the like. Mixtures of polyisocyanates can be used. Preferred monoisocyanates include hexamethylene monoisocyanate, o- and p-toluene monoisocyanate, methylenebis(phenylisocyanate. Preferred diisocyanates include 1-isocyanato-3,3,5-trimethyl-5-isocyanatomethyl cyclohexane (isophorone diisocyanate), 4,4'-diioscyanato dicyclohexylmethane, hexamethylene diisocyanate, 4,4'-diphenylmethane diisocyanate, 4,4'-diphenyl methane diisocyanate (MDI)/1,1'-methylenebis(4-isocyanatobenzene), 2,4'-diphenyl methane diisocyanate (MDI)/1-isocyanato-2-(4-isocyanatophenyl)methylbenzene; 2,2'-diphenyl methane diisocyanate (MDI)/1,1'-methylenebis(2-isocyanatobenzene); 1,6-hexamethylene diisocyanate (HDI)/1,6-diisocyanatohexane.

Chain extenders may also be used in the present invention. The term "chain extender" refers to their function in keratin elastomer synthesis, these compounds provide a bridge between keratin and the isocyanate compound wherein the isocyanate is capable of reacting with the -ol or the -amine groups of the chain extender either sequentially or consecutively with the reaction of these -ol or -amine groups with keratin. Example of such chain lengthening agents containing hydroxyl groups and/or amino groups and/or thiol groups and/or carboxyl groups (preferably hydroxyl groups and/or amino groups and/or thiol groups and/or carboxyl groups (preferably hydroxyl groups and/or amino groups) as low molecular weight polyols and/or amino alcohols with molecular weights of from 62 to 399 (preferably from 62 to 250) such as ethylene glycol; (1,2)- and (1,3)-propanediol, (1,4)- and (2,3)-butanediol; (1,5)-pentanediol; (1,6)-hexanediol; (1,8)-octanediol; neopentyl glycol; 1,4-bis-hydroxymethyl-cyclohexane; 2-methyl-(1,3)-propanediol; dibromobutenediol; dianhydro-hexitols; trimethylolpropane; (1,2,6)-hexanetriol; trimethylolethane; pentaerythritol; quinitol; mannitol and sorbitol; castor oil; di-, tri-, tetra- and higher polyoxyethylene-, polyoxypropylene- and polyoxybutylene-glycols, 1,4-bis-hydroxymethyl-cyclohexane; 2-methyl-(1,3)-propanediol; dibromobutenediol; dianhydro-hexitols; trimethylolpropane; (1,2,6)-hexanetriol; trimethylolethane; pentaerythritol; quinitol; mannitol and sorbitol; castor oil; di-, tri-, tetra- and higher polyoxyethylene-, polyoxypropylene- and polyoxybutylene-glycols, di-, tri- and higher polyoxypropylene glycols; di-, tri- and higher polybutylene glycols; 4,4'-dihydroxydiphenylpropane; dihydroxythyl-hydroquinone; 4,4'-dihydroxydiphenylpropane; dihydroxyethyl-hydroquinone; ethanolamine; diethanolamine; N-methyl-diethanolamine; triethanolamine and 3-aminopropanol, including diamines such as amino,3,5-trimethyl-5-aminomethyl cyclohexane and perhydro-2,4'- and -4,4'-diaminodiphenylmethane. Hydrazine and substituted hydrazines and acid dihydrazides, ethanolamine; diethanolamine; N-methyl-diethanolamine; triethanolamine and 3-aminopropanol. Examples of diamines which may be used as chain lengthening agents include 1-amino-3,3,5-trimethyl-5-aminomethyl cyclohexane and perhydro-2,4'- and -4,4'-diaminodiphenylmethane. Hydrazine and substituted hydrazines and acid dihydrazides may also be used. Aromatic diamine chain lengthening agents include bisanthranilic acid esters; 3,5- and 2,4-diaminobenzoic acid esters; diamines containing ester groups; diamines containing ether groups; 2-halogen-1,3-phenylenediamines optionally substituted in the 5-position; 3,3'-dichloro-4,4'-diamino-diphenylmethane; tolylene diamines; 3,3'-diethyl-5,5'-diisopropyl-diphenylmethane; 4,4'-diaminodiphenylmethane; 4,4'-diaminodiphenylsulfide; diaminodiphenyldithioethers; diaminobenzene phosphonic acid esters; aromatic diamines containing sulfonate or carboxylate groups, and aminoalkylthioanilines, for example, ethanolamine or diethanolamine, preferably as diol, 1,6-hexanediol, cyclohexanedimethylol, and 1,4-butanediol, alkane-1,-2,-3 triols, such as 1,2,3-propanetriol, polyglycerols such as (tri-, hexa-, and decaglycerol, 6 hexanediol, cyclohexanedimethylol, and 1,4-butanediol glycol, polypropylene glycol, and alkanolamines, most preferably a diol, such as amine diol such as ethanolamine and di-, triiethanolamine, and other polyalkanol amines such as tetrakis(2-hydroxypropyl)ethylene diamine, 1,4-bis-(2-hydroxypropyl)2-methylpiperazine, 1,2,4-trimethylpiperazine, glycerol, ethylene glycol, diethylene glycol, triethylene glycol, and polyhydroxy compounds containing three or more hydroxyl groups may be used as chain extenders, and bisanthranilic acid esters; 3,5- and 2,4-diaminobenzoic acid esters; diamines containing ester groups; diamines containing ether groups; 2-halogen-1,3-phenylenediamines optionally substituted in the 5-position; 3,3'-dichloro-4,4'-diamino-diphenylmethane; tolylene diamines; 3,3'-diethyl-5,5'-diisopropyl-diphenylmethane; 4,4'-diaminodiphenylmethane; 4,4'-diaminodiphenylsulfide; diaminodiphenyldithioethers; diaminobenzene phosphonic acid esters; aromatic diamines containing sulfonate or carboxylate groups; aminoalkylthioanilines and polyols containing sulfonate and/or phosphonate groups, preferably the adduct of bisulphite and butane-1,4-diol or the alkoxylation products thereof. Preferred compounds include ethylene glycol; (1,2)- and (1,3)-propanediol, (1,4)- and (2,3)-butanediol; (1,5)-pentanediol; (1,6)-hexanediol; (1,8)-octanediol; neopentyl glycol; 1,4-bis-hydroxymethyl-cyclohexane, amino alcohols with molecular weights of from 62 to 399 (preferably from 62 to 250).

Blocking agents which can be used to from a blocked isocyanate prepolymer can include any suitable aliphatic, cycloaliphatic, or aromatic alkyl monoalcohol or phenolic compound, suitable glycol ethers or oximes, or lactams (U.S. Pat. No. 5,633,297; U.S. Pat. No. 3,923,713), and agents such as, amine- or hydroxyl-functional blocking agents; phenol, ε-caprolactam, benzotriazole, oxime, cyclohexanol, o-, m-, p-cresol, o-, m-, p-methyoxy phenol, p-tertiary butyl phenol, o-nitro phenol, 2-naphthol, 1-nitroso-2-naphthol, 3,5-dimethylpyrazole. Preferred compounds include aliphatic, cycloaliphatic, or aromatic alkyl monoalcohol.

For example, diisocyanate TDI is reacted with phenol to form a monosubstituted precursor, phenyl N-(3-cyanato-4-methylphenyl) carbamate; the phenol reacts (blocks) the more reactive isocyanate (—NCO) group of TDI, leaving one unreacted (unblocked) —NCO group on the TDI aromatic ring. Phenyl N-(3-cyanato-4-methylphenyl) carbamate is then reacted with keratin at room temperature in nonaqueous solvent to form the keratin urethane of phenyl N-(3-cyanato-4-methylphenyl) carbamate. Heat is applied to about 100° to about 120° C. (e.g., 100° to 120° C.) to unblock the phenol-blocked more reactive isocyanate (—NCO) group described above; the product is keratin urethane with —NCO group functionality (meaning that the remaining —NCO can subsequently be reacted with glycol or with any amine, hydroxylamine, alcohol, polyhydric alcohol, as described above). Optionally the keratin urethane may be reacted with polyethylene glycol (400-12,000 MW), ethanol amine, diethanolamine, 1,6-hexanediol, triethanol amine, butanol, anyhdrous glycerol, long chain-polyols. Reactions of keratin urethane will utilize the amino acids functions (amine, carboxyl, thiol, alcohol sulfhydryl, phenolic, guanidine, imidazole, and carboxyl) of the keratin peptide and reactions will be promoted by the typical keratin bonding potentials of electrostatic bonds, hydrogen bonds, hydrophobic interactions, dipole attractions, dispersion forces, and disulfide bonds.

Another method using diisocyanates involves one-step keratin elastomer formation without precursor. [R—(NCO)$_2$ where "R" is an organic moiety] is reacted with keratin (in powder or hydrolysate form) to form keratin elastomer, [K—O—(C=O)—NH—R—NH—(C=O)—O—K]. There are no terminal —NCO groups in the keratin elastomer product, therefore no optional reaction with compounds like glycol is possible.

One method using monoisocyanates involves a one-step keratin elastomer formation without precursor. [R—(NCO)] is reacted with keratin (in powder or hydrolysate form) to form keratin elastomer [K—O—(C=O)—NH—R]. there are no terminal —NCO groups in the keratin elastomer product, therefore no optional reaction with compounds like glycol is possible.

Isocyanate compounds (mono- and di-isocyanates) can thus be used to crosslink keratin by reaction with keratin's hydroxyl and amine groups. The carbamate functional group is formed (R″NHCOOR′) and the product is called keratin carbamate, or keratin urethane, or keratin elastomer.

In the present invention, diisocyanate was blocked with phenol to form a stable prepolymer (precursor) that was subsequently reacted with keratin at the deblocking temperature of the prepolymer; at that temperature the isocyanate group was regenerated to crosslink keratin:

generally the temperature (~100 C.) goes directly over the arrow

Solvents as reaction media which can be utilized include but are not limited to the following: toluene, methylene chloride, ethyl acetate, acetone, methylethyl ketone, dimethylformamide.

We produced a bio-based keratin elastomer and reacted this product with poly(ethylene glycol) through the amino terminus of the keratin protein. Our keratin elastomer can serve as a biopolymer elastomer replacement for various commercial synthetic elastomers and silicones in the cosmetic and hair industries. Keratin urethane is unique in that it presents multiple ionic and polar sites and large molecular surfaces with strong bonding forces, sites for Van der Waals bonding, and hydrogen bonding for important polar interactions and strong binding forces. This material can absorb and desorb onto hair from aqueous solution and will affix to hair with high substantivity. When incorporated into hair and cosmetic compositions the keratin elastomer when chemically or mechanically combined with active agents will affect mammalian skin, hair and nails and will serve aesthetic functions in anti-aging, anti-wrinkling, antioxidation, anti-inflammation, anti-hyperpigmentation, and anti-photoaging. Without being bound by theory, keratin urethane can react with hydroxylated, aminated, amidized, and carboxyl-containing active agents to attach to active ingredients to deliver them to protein substrates, thus the system can serve as a novel delivery agent. The surface energy of this biopolymer elastomer can be tailored to meet needs for hair manageability, smoothness, frictional forces, and cohesion. For example, the skin industry makes use of the natural antioxidant, carotenoid Lutein for termination of free-radical production. Lutein can be incorporated into keratin by reaction of the prepolymer with its end-terminal —OH groups and this product will function as an anti-aging ingredient. In another example, Tretinoin vitamin A can be introduced by reacting the biopolymer precursor with carboxyl-terminal retinoid. The biopolymer can react, with a quaternary polymer to confer antimicrobial efficacy. Also applicable is the attachment of cationic, anionic, or neutral fixatives to hair and skin.

The subject of this invention, keratin urethane, was produced for its biocompatibility and high potential to replace chemically modified carbohydrates (e.g., starch, cellulose, etc.) and for its potential for reactivity to provide high value-added keratin-based materials for cosmetic and biomedical applications.

To this end, for example, we hydrolyzed keratin protein from wool, transformed it into powder, and modified it in situ with phenol-blocked 2,4-toluenediisocyanate (TDI) to form keratin urethane with a blocked site available for subsequent reactivity with polyols. amines, thiols, carboxylic acids and alcohols within a temperature range of 100° C. to 120° C.

where the phenol becomes labile and can be replaced by these chemical constituents, for example by the polyol, polyethylene glycol (PEG).

Unless defined otherwise, all technical and scientific terms used herein have the same meaning as commonly understood by one of ordinary skill in the art to which the invention belongs. The term "about" is defined as plus or minus ten percent; for example, about 100° F. means 90° F. to 110° F. Although any methods and materials similar or equivalent to those described herein can be used in the practice or testing of the present invention, the preferred methods and materials are now described.

The following example are intended only to further illustrate the invention and are not intended to limit the scope of the invention as defined by the claims.

EXAMPLES

Phenol-blocked TDI (phenyl N-(3-cyanato-4-methylphenyl)carbamate):TDI (toluene-2,4-diisocyanate) can act as a homobifunctional reagent that exhibits different reactivities usable in two-step coupling reactions. Keratin to be converted into elastomer was first reacted with TDI as a crosslinker. Unreacted TDI can be removed prior to addition of the second protein or agent. This procedure took advantage of the differential reactivities of functional groups in hetero- and homofunctional reagents as well as their differential selectivities towards the two proteins or reactants to be coupled. Following from the reaction of the —NCO group of phenol-blocked TDI in FIG. 1, keratin reacted at the —NCO site to form keratin urethane, and elastomer. Subsequently keratin urethane was reacted with polyols (e.g., polyethylene glycol of various molecular weights; 12,000 to 300,000) at the phenol-blocked isocyanate site. We used this technology to prepare phenyl N-(3-cyanato-4-methylphenyl) carbamate in toluene.

Figure 4:
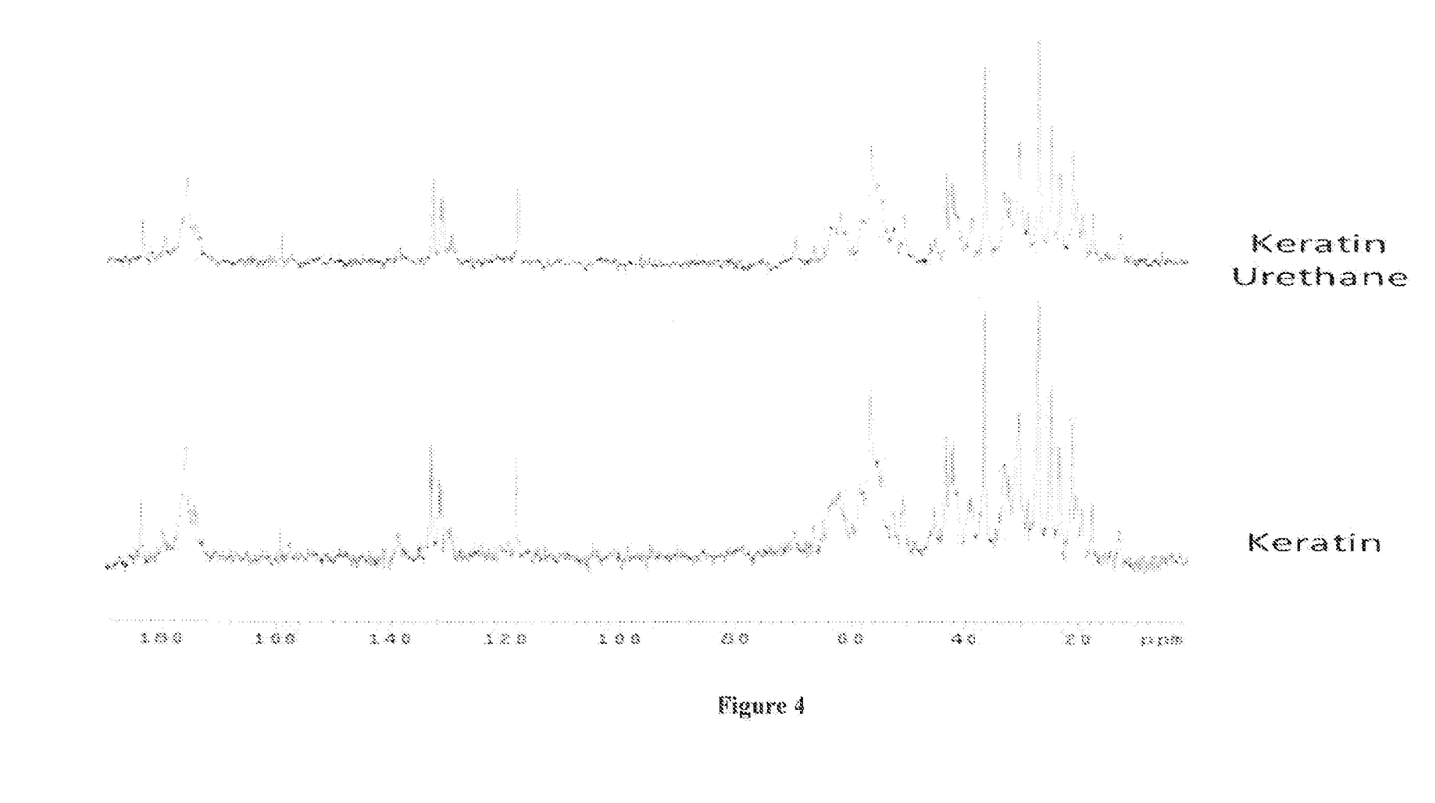
FIG. 4 shows carbon-13 NMR spectra of keratin powder and keratin urethane as described below.

Preparation of keratin powder: To a 1 L/flask were added 30.38 g of wool (degreased by Soxhlet extraction with methylene chloride for 16 h and 600 mL of 0.5N NaOH (12 g NaOH/L). The flask was placed in a shaker incubator and the temperature was adjusted to 60° C. After reacting for three hours the flask was removed and the reaction mixture was centrifuged (250 mL bottles, 10K RPM, 4° C., 30 minutes). The supernatant was decanted from the solids and the supernatant dialyzed against water (Spectra/Por Dialysis tubing, MWCO 6-8,000 Daltons). The ratio of the dialysis water and the solution dialyzed was 10 and the dialysis water was changed after 1 h and then 3×/day. After dialysis the water was removed by lyophilization to yield a white powder that was stored in a dessicator. Keratin hydrolysate lyophilized to white powder was characterized by NMR spectroscopy; the NMR Peaks from scans of $^1$h NMR ppm with TMS as reference were as follows: 1.032 (b, s, Methyl) 1.328, 1.512, 1.746, 2.137, 2.368, 2.79, 3.113, 3.30, 3.88, 3.97, 6.92, 7.22, 7.40, 7.79; $^{13}$C NMR ppm from TMS 13.0 (methyl), 17.6, 19.4, 20.4, 21.2, 23.5, 24.9, 27.0 , 28.9, 30.5, 32.8, 36.3, 38.8, 41.9, 42.4, 43.2, 45.25, 50.7, 52.5, 56.6, 62.0, 64.8, 66.5, 69.6, 118.3, 129.9, 131.45, 131.8, 133.2, 138.7, 157.5, 159.4, 176.1, 180.0, 183.8, IR (cm$^{-1}$) 1238.9, 1312.6, 1398.1, 1449.1, 1529.2, 1653.5, 2875.2, 2933.4, 2961.6, 3068.3, 3309.3. These peak assignments for keratin powder are shown below in FIG. 4 (carbon-13 NMR).

Figure 5:
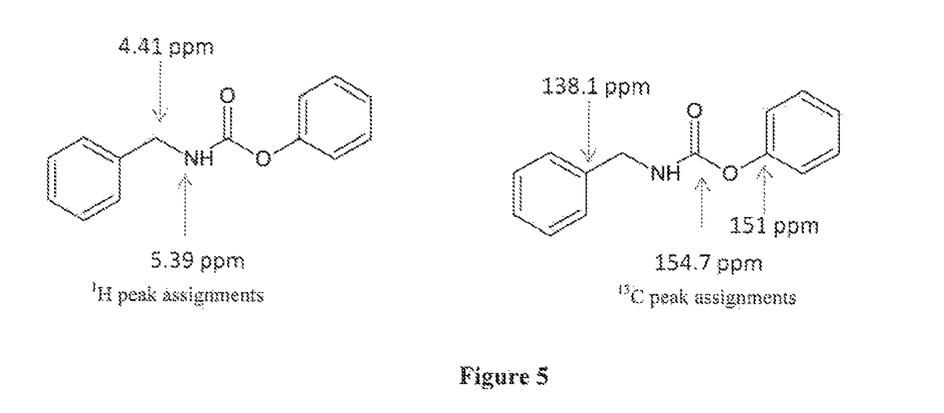
FIG. 5 shows NMR peak assignments for model compound for blocked-TDI: phenyl N-(3-cyanato-4-methlyphenyl)carbamate as described below. Assignment of Selected Peaks in 1H and 13C NMR spectra of model compound, α-phenylurethane of phenol.

Synthesis of model compound (60 -phenylurethane of phenol): To make assignments for NMR spectroscopy, a model compound, α-phenylurethane of phenol, was synthesized and characterized. To a 50 mL Erlenmeyer flask were added 1.2 g phenol, 1 mL of toluene, 0.5 ml of benzylisocyanate and a few drops of pyridine. After 1 hr the reaction was quenched by placing the flask in an ice bath and crystallization was induced by scratching the side of the flask with a glass rod. The crystals were collected by filtration and the product was purified by recrystallization from hot hexane to yield white crystals. Peak assignments were as follows: NMR $^1$H, ppm from TMS, 4.41(d, 2H, φ—CH$_2$—NH—), 5.39p (s, b, 1H, 2H, φ—CH$_2$—NH—), 7.17p(m, 5H, 2H, φ—CH$_2$—NH—), 5.358 (m, 5H, —CH$_2$NH—CO$_2$—φ); $^{13}$C NMR, ppm from TMS, 45.2 (φ—CH$_2$—NH), 121.5, 125.3, 127.665, 128.7, 129.2 (all aromatic ring carbons), 138 (C-1 of aromatic ring bearing methylene groups), 151.0 (C-1 of phenol ring), 154.6 (NH—CO$_2$—φ); IR (cm$^{-1}$) 689.3, 693.3, 715.1, 744.7, 765.0, 778.2, 818.9, 839.2, 914.8, 950.6, 1000.3, 1027.9, 1039.3, 1069.1, 1162.7, 1205.8, 1250.7, 1292.7, 1366.7, 1454.1, 1461.0, 1484.9, 1498.3, 1536.9, 1595.2, 1670.4, 1703.6, 2975.0, 3027.9, 3064.7, 3288.6. These peak assignments are shown below in FIG. 5 (proton and carbon-13 NMR).

Removal of water from phenol: In the formation of phenyl N-(3-cyanato-4-methylphenyl)carbamate, instead of subliming the phenol it was dissolved in toluene and refluxed using a Dean-Stark trap to remove any residual water. Typically only 0.1 to 0.2 mL of water was removed from 30 g phenol.

Synthesis of phenol-blocked TDI (phenyl N-(3-cyanato-4-methylphenyl) carbamate); To a three neck 500 mL round bottom flask equipped with a nitrogen inlet, reflux condenser equipped with a nitrogen outlet, and a 250 mL equal pressure dropping funnel were added 38.82 g (0.223 M) of toluene-2, 4-diisocyanate (TDI), 0.5 mL anhydrous pyridine, and 125 mL anhydrous toluene. The dropping funnel was charged with 23.63 g phenol dissolved in 150 mL of anhydrous toluene. The phenol solution was added to the TDI solution over a period of 12 hr and the mixture was allowed to react an additional 12 hr. The crystals were filtered and the volume of the filtrate was reduced by half to afford a second crop of crystals. The crude product was recrystallized from hot hexane to yield 35.78 g (61% yield). Peak assignments were as follows: NMR 1H, ppm from TMS 1.59 (methyl) 2.28 (methyl) 5.29, 6.94 (NH—CO$_2$—R), 7.101, 7.105, 7.139, 7.153, 7.156, 7.159, 7.164, 7.165, 7.168, 7.176, 7.174, 7.194, 7.202, 7.209, 7.212, 7.218, 7.224, 7.231, 7.242, 7.245, 7.253, 7.257, 7.273, 7.279, 7.286, 7.302, 7.337, 7.339, 7.347, 7.357, 7.360, 7.368, 7.378, 7.386, 7.392, 7.399, 7.408, 7.414, 7.426, 7.435, 7.441, 7.488; $^{13}$C NMR, ppm from TMS 17.7 (methyl), 115.5, 116.2, 121.6, 125.9, 128.4, 129.5, 131.0, 132.9, 136.2, 147.9, 150.5, 151.6. These NMR peak assignments are shown below in FIGS. 2 and 3 (proton and carbon-13, respectively).

Synthesis of Keratin Urethane Product. Reaction of phenyl N-(3-cyanato-4-methylphenyl)carbamate with keratin protein in toluene: to a 125 mL Erlenmeyer flask were added approximately 0.200 mg hydrolyzed wool (2.5×10$^{-5}$ M) and 20 mL anhydrous toluene. The hydrolyzed wool was dispersed in the toluene by placing the flask on a shaker table for 1 hr. To the flask was added a few drops of anhydrous pyridine with 10, 5.0, 2.5 or 1.0 molar excess of phenyl N-(3-cyanato-4-methylphenyl)carbamate and the flask was placed on the shaker table for 12 hrs. The reaction mixture was filtered and dried. Peak assignments were as follows: $^1$H NMR of 5.0 molar excess derivative, ppm from TMS 1.032 (b, s, Methyl) 1.328, 1.512, 1.746, 2.137, 2.368, 2.79, 3.113, 3.30, 3.88, 3.97, 6.92, 7.22, 7.40, 7.79 $^{13}$C NMR spectrum ppm 12.9 (methyl) 17.5, 19.3, 20.3, 21.2, 23.4, 24.9, 27.0, 28.9, 30.4, 32.0, 32.9, 36.3, 38.8, 41.9, 42.4, 43.2, 45.25, 50.6, 52.5, 56.55, 62.0 64.8, 66.4, 69.7, 118.3, 126.3, 131.4, 131.8, 133.2, 138.7, 157.5, 159.4, 176.169, 180.1, 183.8; from TMS IR (cm$^{-1}$) 1238.6, 1312.6, 1398.4, 1534.9, 1655.4, 2875.3, 2962.0, 3305.6. These peak assignments are shown below in FIG. 4 (carbon-13 NMR). The carbon-13 spectra of keratin and keratin urethane in FIG. 4 appeared similar with no clear distinctions due to the large differential between the molecular weights of keratin (~8,000 kDa) and phenyl N-(3-cyanato-4-methylphenyl)carbamate (268.5 Da).

Synthesis of keratin urethane polyol product. Reaction of the reaction product of phenyl N-(3-cyanato-4-methylphenyl)carbamate with hydrolyzed keratin and PEG (keratin PEG dicarbamate): to a 125 mL Erlenmeyer flask was added approximately 0.200 gm of keratin (ARS-2), 20 mL anhydrous DMF and a couple of drops of anhydrous pyridine. To this was added 0.007 g ($2.61 \times 10^{-5}$ M phenyl N-(3-cyanato-4-methylphenyl)carbamate. The reaction mixture was stirred for 3 h after which time all of the hydrolyzed wool has dissolved. This mixture was added to a 250 mL round bottom flask equipped with a reflux condenser. To the mixture was added 20 mL anhydrous DMF containing 0.0198 g ($4.95 \times 10^{-5}$ M) PEG (MW≈400) and a couple of drops of dibutyltin dilaurate. The reaction mixture was heated for 4 h at 105±2° C. The mixture was cooled to room temperature to yield a pale yellow solvent that was insoluble in DMF and $H_2O$. See FTIR absorption in FIG. 8: IR ($cm^{-1}$) 1098.9, 1234.6, 1311.8, 1388.7, 1440.9, 1535.8, 1661.8, 2873.5, 2931.9, 2959.3.

Results and discussion. NMR α-Phenylurethane of phenol (model compound): Model compound α-Phenylurethane of phenol, was synthesized as its $^1H$ and 13C NMR spectra would aid in the assignment of the $^1H$ and $^{13}C$ NMR spectra of phenyl N-(3-cyanato-4-methylphenyl)carbamate. The partial assignment of the $^1H$ and $^{13}C$ NMR spectra of the α-phenylurethane are given in FIG. 5. The proton NMR spectrum contained a peak at 5.39 ppm which was assigned to the protonated amine. The appearance of this peak in the NMR spectrum confirmed that α-phenylurethane of phenol was synthesized. Additional supporting evidence was the splitting of the $CH_2$ peak by this same proton ($J_{H-H}$=6.26 Hz). The peaks of interest in the $^{13}C$ NMR spectrum of the α-phenylurethane were the non-protonated peaks. One of these peaks arose from the formation of the carbamate.

Phenyl N-(3-cyanato-4-methylphenyl)carbamate (precursor to keratin urethane product, blocked TDI): Phenyl N-(3-cyanato-4-methylphenyl)carbamate was very soluble so a minimal amount of toluene was used for the reaction. The product was dissolved in a minimal amount of chloroform and precipitated by the addition of hexane. Then the product was recrystallized from hexane.

Figure 2:
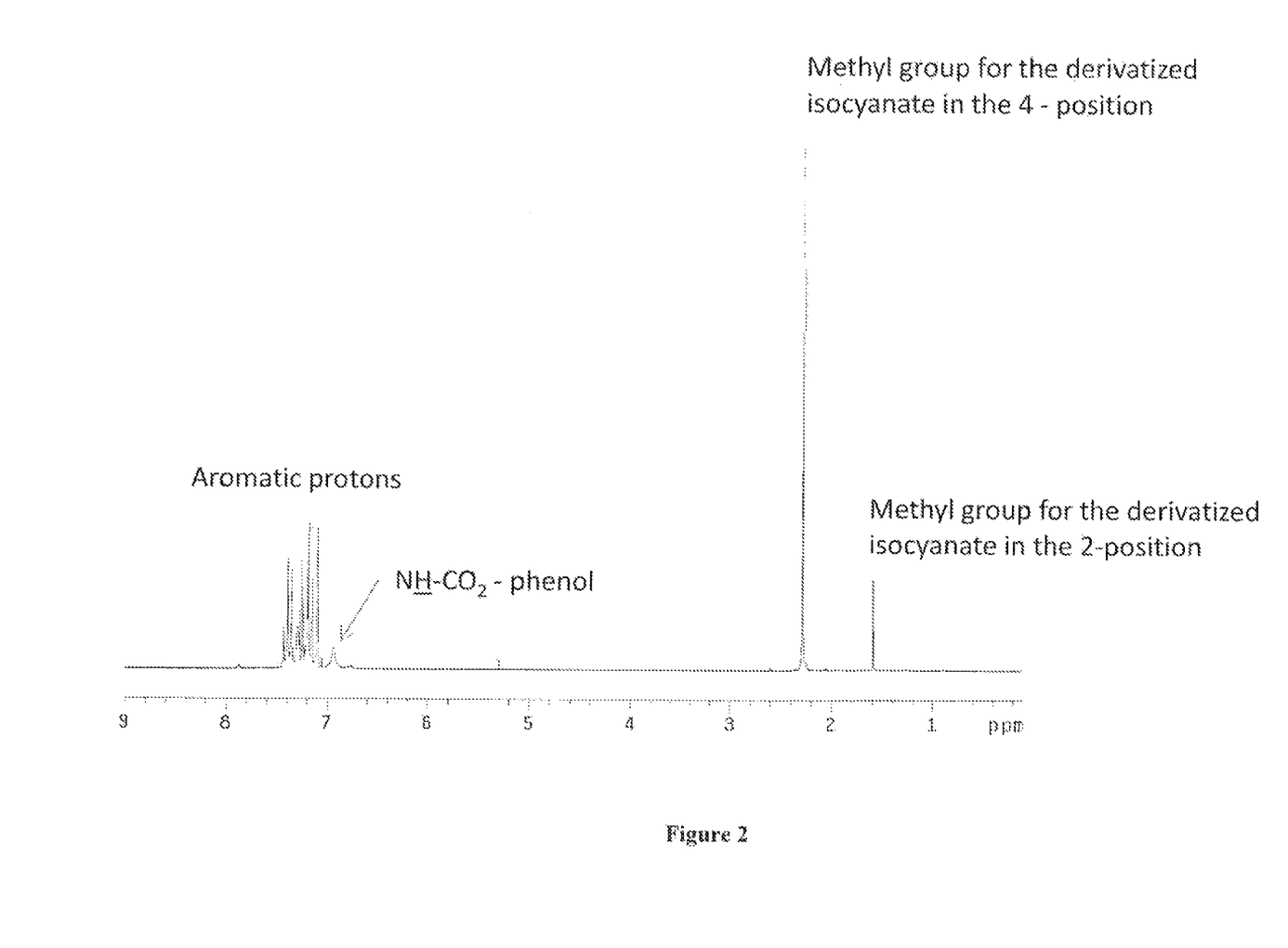
FIG. 2 shows proton NMR of phenol-blocked TDI (phenyl N-(3-cyanato-4-methlyphenyl)carbamate) as described below.
Figure 3:
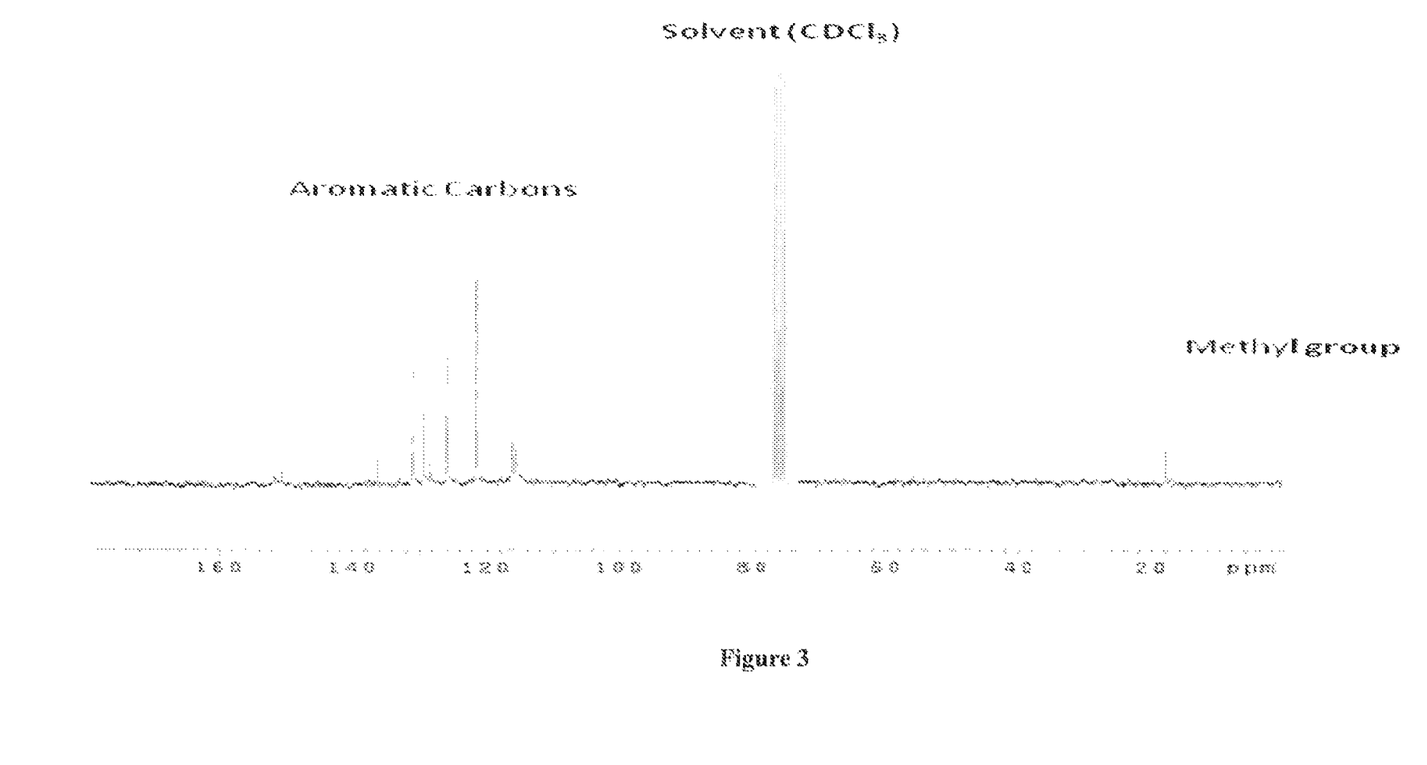
FIG. 3 shows carbon-13 NMR of phenol-blocked TDI (phenyl N-(3-cyanato-4-methlyphenyl)carbamate) as described below.
Figure 6:
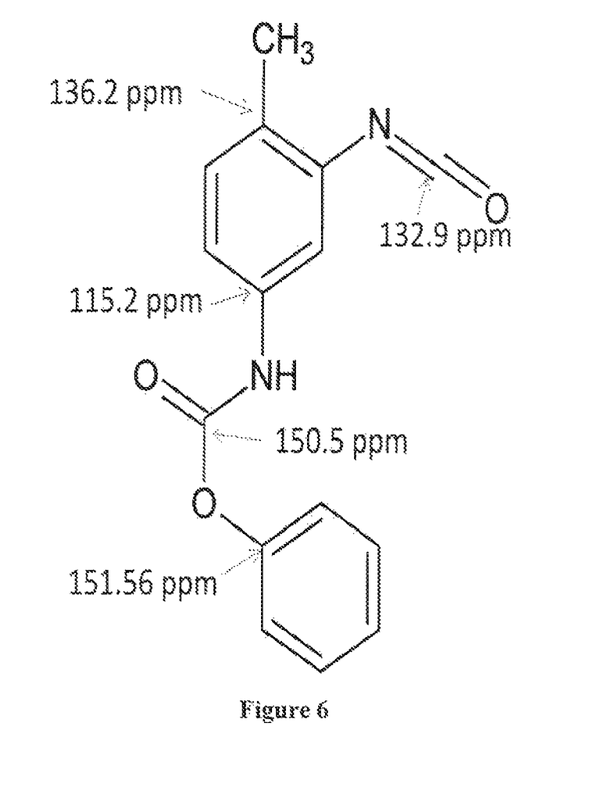
FIG. 6 shows carbon-13 NMR peak assignments of phenyl N-(3-cyanato-4-methlyphenyl)carbamate as described below.

Both the $^1H$ and $^{13}C$ NMR spectra were complex as shown in FIGS. 2 and 3. The $^1H$ NMR spectrum contained a peak of 6.94 ppm which was from the protonated nitrogen present in the carbamate. The $^1H$ NMR spectrum also contained 2 methyl peaks (1.59 and 2.28 ppm). The proton spectrum of the starting material (toluene-2,4 diisocyanate) contained only one methyl peak at 2.26 ppm, thus the spectrum of blocked TDI was different from the TDI starting material. Without being bound by theory, from stereo hindrance consideration one would expect a smaller amount of the 2-isocyanate derivative in blocked TDT. Based on integration the ratio of the two peaks the ratio of the 4-isocyanate derivative to the 2-isocyanate derivative was approximately 8 to 1. The aromatic proton peaks for the phenolic ring were separated from the aromatic protons of the diisocyanate, however no attempt was made to assign these peaks. The corresponding carbon-13 spectrum assignments are shown in FIG. 6.

Mass spectrometry of phenol-blocked diisocyanate precursor to keratin urethane product: Phenyl N-(3-cyanato-4-methlyphenyl)carbamate. The mass spectrum of this sample was obtained on a GC-MS spectrometer. The temperature of the injection port was greater than 200° C,. Phenyl N-(3-cyanato-4-methlyphenyl) decomposed at temperatures greater than 100° C. The GC-MS trace contained two peaks: one with a retention time of 5.651 to 6.202 min and a second peak with a retention time of 9.328 to 9.971 min. The mass spectrum identified the material in the first peak as phenol and the material in the second peak as toluene 2,4 diisocyanate.

Figure 7:
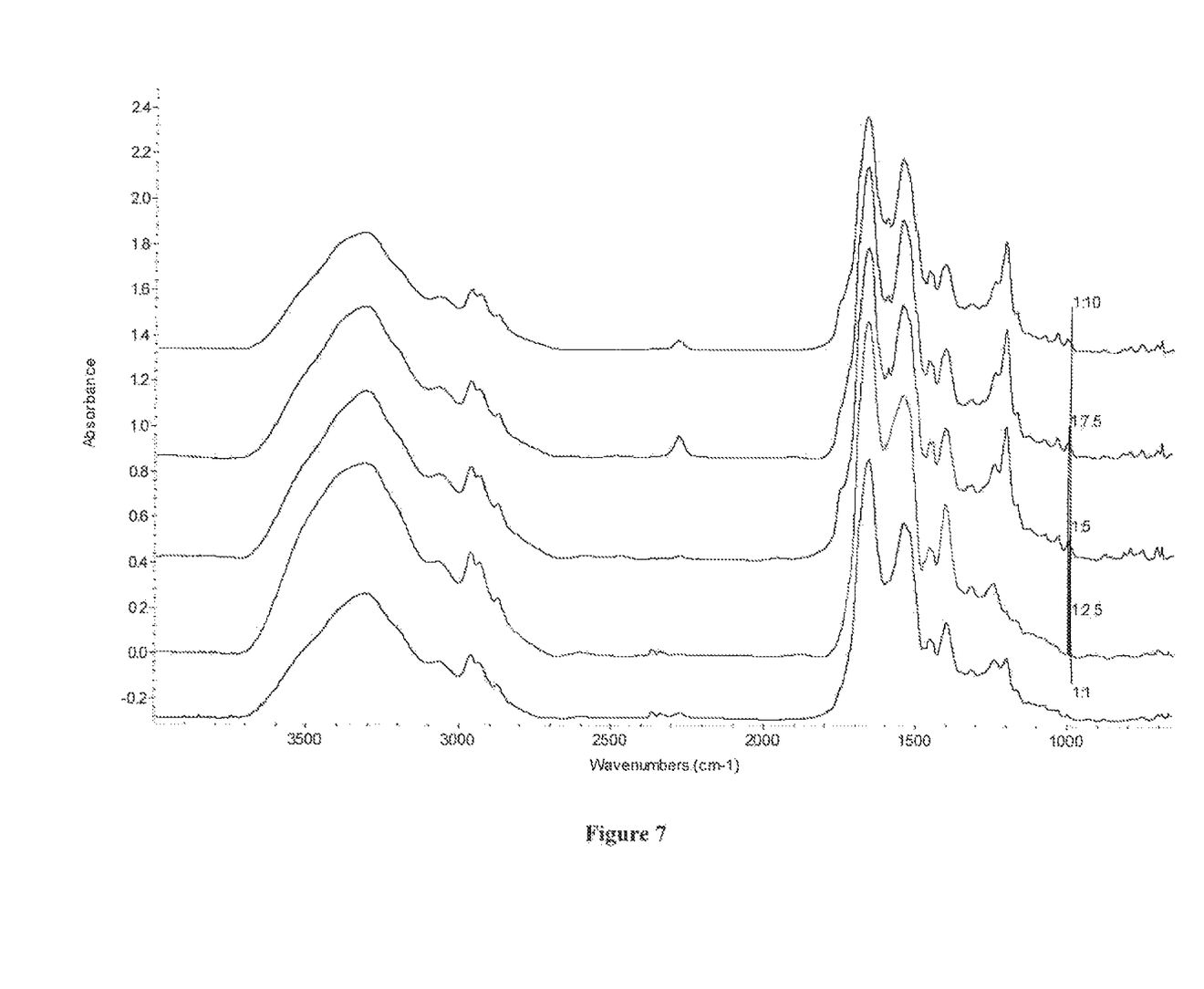
FIG. 7 shows phenol-blocked TDI (phenyl N-(3-cyanato-4-methlyphenyl): FTIR ($cm^{-1}$) absorption peaks, as described below, are as follows: 689.6, 702.5, 715.4, 801.3, 850.7, 863.9, ,996.7, 1031.9,, 1078.9, 1155.7, 1202.4, 1239.1, 1299.9, 1385.5, 1457.0, 1478.0, 1522.8, 1548.6, 1596.7, 1609.2, 1704.6, 1730.5, 2257.9, 3272.5.

FTIR: A series of reactions were run to determine the maximum amount of phenyl N-(3-cyanato-4-methlyphenyl) carbamate that will react with keratin protein (see FIG. 7). The amount of phenyl N-(3-cyanato-4-methlyphenyl) used in this series of reactions was based on the assumption that the average molecular weight of the keratin protein was 8,000 Daltons as determined by gel electrophoresis analysis. The amounts of keratin to phenyl N-(3-cyanato-4-methlyphenyl) were 1:10, 1:75, 1:5, and 1:25, and 1:1 molar ratios shown in the FTIR spectra below. Optimized reaction conditions were with 1:5 keratin to phenyl N-(3-cyanato-4-methlyphenyl) and the reaction was rapid at room temperature, reaching completion in less than 3 h with no residual cyano groups at 2270 $cm^{-1}$ as shown in the FTIR spectrum in FIG. 7.

Figure 8:
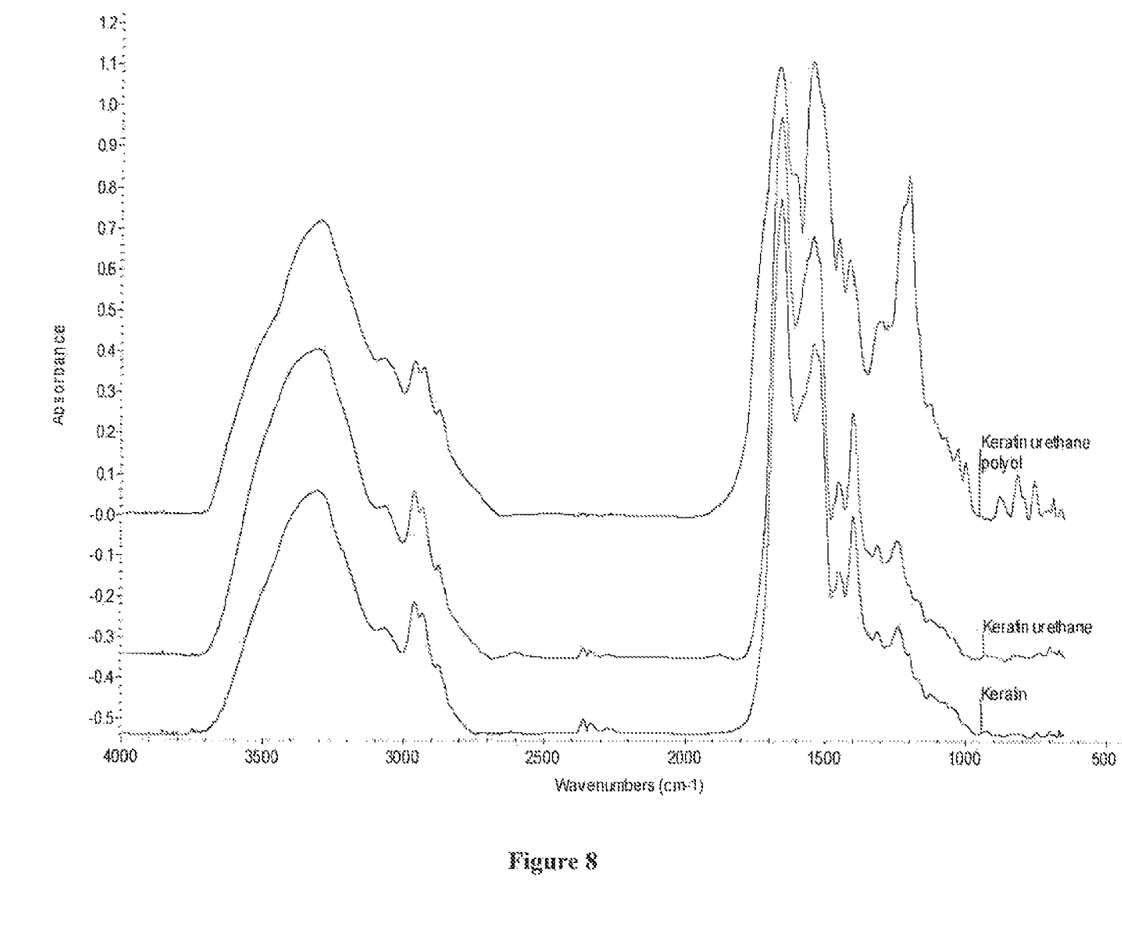
FIG. 8 shows FTIR spectra: keratin powder (bottom spectrum), keratin urethane (middle), and final product (keratin elastomer (keratin urethane polyol)) (top) as described below.

In FIG. 8, the assignment of peaks in the IR spectrum of keratin urethane were as follows ($cm^{-1}$): 1238.6 C—O or C—S, 1312.6, C—O, 1398.4 unknown, 1398.6 and 1534.9 Amide II, 1655.4 Amide I, 3068, 2962, 2936.2 and 2875.3 C—H and broad peak centered at 3305.6 was hydroxyl. The increase in the —OH region at 3300 cm–1 and the very strong peak at in the 1200-1015 region indicated C—O absorption from ester formation of PEG with keratin urethane at the labile phenol site, and any free unreacted —OH groups on the polyol bound to the keratin urethane.

Conclusions: Keratin from wool was converted to keratin elastomer by the chemical reaction of keratin with isocyanates to form urethane linkages. Keratin elastomer was formed from a prepolymer, phenyl N-(3-cyanato 4 methyl phenyl) carbamate, the produce of the reaction of 1:1 molar ratio phenol to toluene diisocyanate (TDI) whereby TDI's 2-position isocyanate (—NCO) group was blocked but the 4-position —NCO remained labile for subsequent reaction with phenol to from carbamate linkages (keratin urethane functions). The formed keratin elastomer (urethane) contained an end group isocyanate as the site of potential reactivity with polyhydric, polyamino, or polycarboxy compound constituents of active agents. We used a polyol, PEG, as proof of concept to form keratin urethane polyol.

We foresee the advantage of keratin urethane compositions over silicone-derived compositions. keratin elastomer can form topical microemulsion, hydrogel, foam, ointment plaster, suspension, and cream with no odor and with aesthetically pleasing appearance. Keratin, like silicone can impart silky, supple feel, yet keratin has the potential for broad reactivity, including the chelation with metals and colorants leading to improvement in color absorption and stability for dyed and tinted hair and skin. Unlike silicon emulsion, keratin emulsion can be dyed and easily affixed to proteinaceous substrates, for example, in dyeing and staining while presumably imparting shiny color and smooth texture. Furthermore, keratin-based elastomers can be composed for style-retention-manageability by engineering hydrophilic/hydrophobic character to modulate low fiber friction and cohesive forces between fibers. The surface energy of keratin elastomer can be tailored to meet needs for hair manageability, smoothness, frictional forces, and cohesion. There are various product development possibilities for a keratin elastomeric system. When applied as a continuous film, tailored biopolymer elastomer can be made to produce tightening while maintaining an active ingredient's contact with the skin. Biopolymer-in-water emulsion can replace silicone-in-water emulsion and it can be designed to hold retinoids on the skin to produce cheek and under-eye firmness, improved cheek and jawl contour, and reduction in fine lines and wrinkles. Keratin elastomer will be composed in various forms for topical applications. The selective chemical reactivity of this produce has direct implications for the design of value-added keratin compositions, for stand-alone cosmetics and hair products, and as a vehicle for delivering active ingredients in compositions. The market potential and impact of keratin elastomer could be significant.

All of the references cited herein, including U.S. Patents, are incorporated by reference in their entirety. Also incorporated by reference in their entirety are the following references: JP2002309488; EP 1,353,005; U.S. Pat. No. 4,144,027; U.S. Patent Application Publication 2006/0233731; JP2006348015 (U.S. 20060088493); JP2003212724 (U.S. 20030161806)); U.S. Pat. No. 4,895,722; U.S. Pat. No. 6,914,126; U.S. Pat. No. 7,001,988; Barr, T., et al., J. Society of Dyers and Colorists, 62(11): 338-345 (1946)); Cardamone, J. M., Lignin Polyurethane as Durable Press Finishing Agent, In: Proceedings of the AATCC International Conference, Philadelphia, Pa., 154-162, 1989; Cardamone, J. M., Textile Research J., 62(7): 371-381 (1992)); Colthup, N. B., et al., Introduction to Infrared and Raman Spectroscopy, Academic Press, New York, 274; Fraenkel-Conrat, H., et al., J. Am. Chem. Soc., 67(2): 314-319 (1945)); Freddi, G., et al., J. Applied Polymer Sci., 89: 1390-1396 (2003); Gaertner, H. F. and R. E. Offord, Bioconjugate Chem., 7: 38-44 (1996)); Hunton, E. H., Textile Research Journal, 44 (4): 233-292 (1974); Lamber, J. B., et al., Organic Structural Analysis, Macmillian Publishing Co., New York, 1976, pg. 240; Schick, A. F., and S. J. Singer, J. Biol. Chem., 236(9): 2477-2485 (1961).

Thus, in view of the above, the present invention concerns (in part) the following:

A method to produce keratin elastomer, said method comprising (or consisting essentially of or consisting of):

(A)(1) reacting a diisocyanate with a blocking agent to form a diisocyanate with one —NCO group blocked by the blocking agent and one —NCO group unblocked, (2) reacting the diisocyanate with one —NCO group blocked by the blocking agent and one —NCO group unblocked with keratin at about 100° to about 120° C. to form keratin urethane with —NCO group functionality (i.e., with one —NCO group unblocked), (3) optionally reacting the keratin urethane with —NCO group functionality with a compound capable of reacting with the —NCO group;

(B) reacting a diisocyanate with keratin to form keratin elastomer; or (C) reacting a monoisocyanate with keratin to form keratin elastomer.

The above method, wherein said method comprises (1) reacting a diisocyanate with a blocking agent to form a diisocyanate with one —NCO group blocked by said blocking agent and one —NCO group unblocked, (2) reacting said diisocyanate with one —NCO group blocked by said blocking agent and one —NCO group unblocked with keratin at about 100° to about 120° C. to form keratin urethane with —NCO group functionality, and (3) optionally reacting said keratin urethane with —NCO group functionality with a compound capable of reacting with said —NCO group.

The above method, wherein said method comprises)(1) reacting a diisocyanate with a blocking agent to form a diisocyanate with one —NCO group blocked by said blocking agent and one —NCO group unblocked, (2) reacting said diisocyanate with one —NCO group blocked by said blocking agent and one —NCO group unblocked with keratin at about 100° to about 120° C. to form keratin urethane with —NCO group functionality, and (3) reacting said keratin urethane with —NCO group functionality with a compound capable of reacting with said —NCO group.

The above method, wherein said method comprises reacting a monoisocyanate with keratin to form keratin elastomer.

The above method, wherein said diisocyanate is toluene diisocyanate.

The above method, wherein said blocking agent is phenol.

The above method, wherein said diisocyanate with one —NCO group blocked by said blocking agent and one —NCO group unblocked is phenyl N-(3-cyanato-4-methylphenyl)carbamate.

The above method, wherein said keratin is in powder or hydrolysate form.

Keratin elastomer produced by the above method.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

I claim:

1. A method to produce keratin elastomer, said method comprising:
   (1) reacting a diisocyanate with a blocking agent to form a diisocyanate having one —NCO group blocked by said blocking agent and one —NCO group unblocked,
   (2) reacting said diisocyanate having one —NCO group blocked by said blocking agent and one NCO group unblocked with keratin to form keratin urethane having one —NCO group blocked by said blocking agent,
   (3) then heating said keratin urethane having one —NCO group blocked by said blocking agent at about 100° to about 120° C. to form keratin urethane having —NCO group functionality, and
   (4) reacting said keratin urethane having —NCO group functionality with polyols or polyhydric alcohols to form keratin elastomer; wherein said keratin is in powder or hydrolysate form; and wherein said blocking agent is phenol.

2. The method according to claim 1, wherein said diisocyanate is toluene diisocyanate.

3. The method according to claim 1, wherein said diisocyanate having one —NCO group blocked by said blocking agent and one —NCO group unblocked is phenyl N-(3-cyanato-4-methylphenyl)carbamate.

4. The method according to claim 1, wherein the polyol is polyethylene glycol.

5. The method according to claim 1, said method comprising reacting a 1 to 10 fold molar excess of said diisocyanate having one —NCO group blocked by said blocking agent and one —NCO group unblocked with keratin to form keratin urethane having one —NCO group blocked by said blocking agent.

6. The method according to claim 1, said method comprising reacting a 1 fold molar excess of said diisocyanate having one —NCO group blocked by said blocking agent and one —NCO group unblocked with keratin to form keratin urethane having one —NCO group blocked by said blocking agent.

7. The method according to claim 1, said method comprising reacting a 2.5 fold molar excess of said diisocyanate having one —NCO group blocked by said blocking agent and one —NCO group unblocked with keratin to form keratin urethane having one —NCO group blocked by said blocking agent.

8. The method according to claim 1, said method comprising reacting a 5 fold molar excess of said diisocyanate having one —NCO group blocked by said blocking agent and one —NCO group unblocked with keratin to form keratin urethane having one —NCO group blocked by said blocking agent.

9. The method according to claim 1, said method comprising reacting a 10 fold molar excess of said diisocyanate having one —NCO group blocked by said blocking agent and one —NCO group unblocked with keratin to form keratin urethane having one —NCO group blocked by said blocking agent.

\* \* \* \* \*